United States Patent
Schelges et al.

(12)

(10) Patent No.: US 6,391,834 B1
(45) Date of Patent: May 21, 2002

(54) FOAMING BODY-CLEANSING AGENTS

(75) Inventors: Heike Schelges; Wolfhard Scholz; Gryta Schosser, all of Krefeld (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/319,192

(22) PCT Filed: Nov. 24, 1997

(86) PCT No.: PCT/EP97/06556

§ 371 Date: Jun. 2, 1999

§ 102(e) Date: Jun. 2, 1999

(87) PCT Pub. No.: WO98/24409

PCT Pub. Date: Jun. 11, 1998

(30) Foreign Application Priority Data

Dec. 2, 1996 (DE) .......................... 196 49 895

(51) Int. Cl.$^7$ ........................ A61K 7/075; A61K 7/50
(52) U.S. Cl. ................ 510/123; 510/119; 510/125; 510/126; 510/130; 516/203
(58) Field of Search ................ 510/119, 123, 510/125, 126, 130; 516/203

(56) References Cited

U.S. PATENT DOCUMENTS

| 5,578,560 | A | * | 11/1996 | Giesen et al. ................. 510/237 |
| 5,653,970 | A | * | 8/1997 | Vermeer .................... 424/70.24 |
| 5,656,200 | A | * | 8/1997 | Boettcher et al. ............ 252/307 |
| 5,858,957 | A | * | 1/1999 | Donoghue et al. ........... 510/445 |
| 5,883,068 | A | * | 3/1999 | Hensen et al. ............... 510/427 |
| 5,981,452 | A | * | 11/1999 | Schrader et al. ............. 510/151 |
| 6,087,320 | A | * | 7/2000 | Urfer et al. .................. 510/470 |

FOREIGN PATENT DOCUMENTS

| DE | 41 31 992 | 4/1993 |
| DE | 42 34 487 | 4/1994 |
| DE | 43 01 820 | 7/1994 |
| DE | 44 35 387 | 4/1996 |

* cited by examiner

*Primary Examiner*—Jill Warden
*Assistant Examiner*—LaToya Cross
(74) *Attorney, Agent, or Firm*—Stephen D. Harper; Kimberly R. Hild; Glenn E. J. Murphy

(57) ABSTRACT

A foaming aqueous body-cleansing composition of (a) an anionic surfactant, (b) an alkyl (oligo)glycoside, (c) a zwitterionic surfactant, (d) an ampholytic surfactant is presented. The body cleansing composition produces a stable, fine-bubble, creamy-feeling foam.

9 Claims, No Drawings

FOAMING BODY-CLEANSING AGENTS

This application filed under 35 U.S.C. 371 and based on PCT/EP97/06556, filed Dec. 2, 1996.

BACKGROUND OF INVENTION

1. Field of the Invention

This invention relates to foaming body-cleansing compositions in the form of a liquid surfactant composition based on a combination of high-foaming anionic surfactants and foam-boosting alkyl (poly)glycosides which contain a combination of a zwitterionic surfactant and an ampholytic surfactant for further improving the properties of the foam, more particularly its fine-bubble character and its stability (creaminess).

Liquid body-cleansing compositions which are marketed, for example, as liquid soaps, shampoos, shower bath preparations and foam bath additives are not only expected to have a good cleansing effect, they are also expected to show high skin and mucous membrane compatibility and not to overly degrease or dry the skin, even in the event of frequent use. In addition to this, however, consumers also evaluate performance properties according to the quality and quantity of the foam formed in use. In particular, consumers look for rapid initial foaming with formation of a fine-bubble and stable foam, these properties of the foam also being generally described as creaminess.

The body-cleansing formulations themselves are also expected to be distinguished by a certain viscosity so that, for example, they can be applied to the hand and do not trickle through the fingers before they can be spread over the body or the head.

There are many known surfactants which are kind to the skin and compatible with the mucous membrane. However, there are only a few surfactants which meet the additional need for a certain viscosity of the aqueous solution and for a fine-bubble character of the foam. For this reason, combinations of various surfactants have always been used hitherto in order to satisfy these various requirements. Thus, a combination of alkyl ether sulfate surfactants and alkyl (poly)glucosides has proved to be particularly high-foaming and dermatologically compatible. In addition, zwitterionic surfactants or betaine surfactants and ampholytic surfactants are known for their ability, in combination with anionic surfactants, to improve the dermatological compatibility of those surfactants and to impart a relatively high viscosity to aqueous preparations or to improve their thickenability by electrolyte salts.

2. Discussion of Related Art

DE-A-42 34 487, for example, describes an aqueous detergent composition containing alkyl sulfate surfactants, alkyl ether sulfate surfactants, alkyl (oligo)glucosides and amphoteric or zwitterionic surfactants.

However, it has now been found that the properties of the foam, more especially its fine-bubble character and stability, can be further improved by using a combination of a zwitterionic surfactant and an ampholytic surfactant instead of a betaine surfactant or ampholytic surfactant.

DESCRIPTION OF THE INVENTION

Accordingly, the present invention relates to aqueous body-cleansing compositions containing high-foaming, dermatologically compatible anionic surfactants (A) and alkyl (oligo)glycosides (B), characterized in that they contain a combination of a zwitterionic surfactant (C) corresponding to formula I:

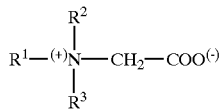

and an ampholytic surfactant (D) corresponding to formula II:

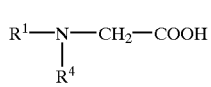

in which $R^1$ is an alkyl or alkenyl group containing 12 to 18 carbon atoms or a group $R^5-CONH-(CH_2)_n$, where $R^5$ is an alkyl or alkenyl group containing 12 to 18 carbon atoms and n is a number of 2 to 4, and $R^2$, $R^3$ and $R^4$ are alkyl groups containing 1 to 4 carbon atoms or hydroxyalkyl groups containing 2 or 3 carbon atoms, in a ratio by weight of (A) to (B) to (C+D) of 10:(0.5–5):(1–5)

in order further to improve their foam properties and their viscosity.

High-foaming, dermatologically compatible anionic surfactants (A) are known to the expert in large numbers from relevant handbooks and are commercially available. More particularly, they are alkyl sulfates in the form of their ammonium or alkanolammonium salts, alkyl ether sulfates, alkyl ether carboxylates, acyl isethionates, acyl sarcosinates, acyl taurines with linear alkyl or acyl groups containing 12 to 18 carbon atoms and in the form of their alkali metal or ammonium salts. The anionic surfactants (A) may be present in the compositions according to the invention in a quantity of 3 to 30% by weight. Particularly preferred anionic surfactants are alkyl ether sulfates. Accordingly, at least one alkyl ether sulfate surfactant corresponding to the formula III:

in which $R^6$ is an alkyl or alkenyl group containing 12 to 18 carbon atoms, m=1–4 and $M^{(+)}$ is an alkali metal, magnesium, ammonium or alkanol-ammonium ion, is preferably present as the anionic surfactant in a quantity of at least 5% by weight, based on the composition as a whole.

Alkyl (oligo)glycosides (B) are well-known surface-active substances which can be produced from sugars and aliphatic primary alcohols containing 8 to 22 carbon atoms by acetalization. Sugar components (glycoses) include—preferably—glucose and also fructose, mannose, galactose, talose, gulose, allose, idose, arabinose, xylose, lyxose, ribose and mixtures thereof. The acetalization products of glucose with fatty alcohols obtainable, for example, from natural oils and fats by known methods are preferably used by virtue of their ready accessibility and their favorable applicational properties.

So far as the glycoside unit is concerned, both monoglycosides and oligoglycosides where a sugar unit is attached to the fatty alcohol by a glycosidic bond are suitable. Mixtures of mono- and oligoglucosides are usually present in the commercially available products.

Preferred alkyl (oligo)glycosides (B) are those with the formula $R^7(G)_x$, where $R^7$ is a linear alkyl group containing 8 to 16 carbon atoms and $(G)_x$ is an (oligo)glucoside unit with an average degree of oligomerization x of 1 to 2.

Such products are commercially available, for example, under the trade mark Plantaren® or Plantacare®.

Zwitterionic surfactants (C) corresponding to formula I are also well-known and are commercially available in large numbers. The most well-known and most widely used group of these surfactants are the betaine surfactants in which $R^2$ and $R^3$ are methyl groups. Among the betaine surfactants, there are the alkyl betaines where $R^1$ is an alkyl or alkenyl group and the amidobetaines where $R^1$ is a group $R^5CONH-(CH_2)_n-$. A cocoamidopropyl betaine of formula I, where $R^1$ is a group $R^5CONH-(CH_2)_3-$, in which $R^5CO$ is derived from a $C_{12-18}$ cocofatty acid or palm kernel oil fatty acid, and $R^2$ and $R^3$ are methyl groups, is preferably used for the purposes of the invention. Such products are commercially available, for example, under the trade mark Dehyton®K.

Ampholytic surfactants (D) corresponding to formula II are also known and commercially available surfactants. They have the ability to react like cationic surfactants in acidic solution by protonation at the tertiary nitrogen atom and like anionic surfactants in the alkaline range by salt formation at the carboxyl group. A preferred ampholytic surfactant (D) is a cocoamphoglycinate corresponding to formula II where $R^1$ is a group $R^5CONH-(CH_2)_2-$, in which $R^5CO$ is derived from a $C_{12-18}$ cocofatty acid or palm kernel oil fatty acid, and $R^4$ is a hydroxyethyl group. One such surfactant is commercially available, for example, under the trade mark Dehyton®G.

Particularly favorable foam properties, more especially fine bubbles and creaminess, are obtained when the zwitterionic surfactant (C) and the ampholytic surfactant (D) are present in a ratio by weight of (C) to (D) of 1:(0.1–0.5).

Besides the compulsory components (A), (B), (C) and (D), the foaming aqueous preparations according to the invention may also contain other surfactants and additives. In quantitative terms, these other ingredients together should not make up any more than component (A).

Suitable other additives are, for example, nonionic surfactants, water-soluble polymers, for example cationic polymeric conditioners, pearlescers, dyes, fragrances and emulsifiers suitable therefor, water-soluble polyols such as, for example, glycerol, sorbitol, propylene glycol or polyethylene glycol, electrolyte salts, pH regulators and cosmetic or dermatological agents.

If the total content of components (A) and (B) is less than 10% by weight, the viscosity of body-cleansing compositions according to the invention may still be unsatisfactory. One particular advantage of the compositions according to the Invention is that, in cases such as these, viscosity can readily be increased by the addition of water-soluble inorganic electrolyte salts.

Suitable inorganic electrolyte salts are any water-soluble alkali metal, ammonium and alkaline earth metal salts, for example the fluorides, chlorides, bromides, sulfates, phosphates, nitrates and hydrogen carbonates, providing they are soluble in water at 20° C. in a quantity of at least 1% by weight. Sodium chloride and magnesium chloride are preferably used.

The body-cleansing compositions according to the invention may be formulated as highly concentrated pastes with a water content of less than 30% by weight $H_2O$ or as dilute aqueous solutions containing less than 5% by weight of the anionic surfactant (A). However, the content of anionic surfactants (A) is preferably in the range from 5 to 20% by weight In this range, body-cleansing compositions according to the Invention suitable for use as shampoos or shower gels can be formulated with viscosities in the range from about 1 to 200 Pa·s(20° C.).

The following Examples are intended to illustrate the invention:

EXAMPLES

I. Surfactants Used

| | |
|---|---|
| Texapon ®N70: | $C_{12/14}$ cocofatty alcohol-2 EO-adduct sulfate, Na salt (70% paste) |
| Dehyton ®K: | Cocoamidopropyl Betaine (30% solution)<br>(+)      (−)<br>$R-CONH-(CH_2)_3-N(CH_3)_2-CH_2\ COO$<br>$R^1CO$ = acyl group of $C_{8-18}$ cocofatty acid |
| Dehyton ®G: | Cocoamphocarboxyglycinate (30% solution)<br>$R^2-CONH-(CH_2)_3-NH(CH_2CH_2OH)$<br>$CH_2-COOH$<br>$R^2CO$ = acyl group of $C_{8-18}$ cocofatty acid |
| Plantacare ®818: | $C_{8-14}$ alkyl polyglucoside (50% solution)<br>$R^3-(G)_x$, $R^3 = C_{8-14}$-n-alkyl group<br>x = 1.4 G = glucoside unit |
| Cetiol ®HE: | PEG7 Glyceryl Cocoate |
| Euperian ®PK 810: | Pearlescing concentrate containing glycol distearate and Texapon N70. |

II. Evaluation of Foam Volume and Quality

Foaming behavior and foam properties were tested in a standardized arm washing test. 2 g of the composition were applied to the wet hand and spread over the hands and forearms. After 1 minute, the composition was washed off with water (15° C.). Foaming behavior, foam volume and creaminess were evaluated by ten examiners. Their scores were averaged (1=poor, 2=adequate, 3=good, 4=very good).

Formulations

| % by weight | 1 | 2V | 3V | 4V | 5V | 6V |
|---|---|---|---|---|---|---|
| Texapon N 70 | 15 | 15 | 15 | 17 | 18 | 16 |
| Plantaren 818 | 2 | 2 | 2 | 4 | — | — |
| Dehyton K | 6 | 8 | — | — | — | 6 |
| Dehyton G | 2 | — | 8 | — | 2 | 2 |
| Eurperlan PK 810 | 2 | 2 | 2 | 2 | 2 | 2 |
| Cetiol HE | 0.5 | 0.5 | 0.5 | 0.5 | 0.5 | 0.5 |
| Merquat 550 | 0.5 | 0.5 | 0.5 | 0.5 | 0.5 | 0.5 |
| Sorbitol | 1.5 | 1.5 | 1.5 | 1.5 | 1.5 | 1.5 |
| Glycerol | 1.0 | 1.0 | 1.0 | 1.0 | 1.0 | 1.0 |
| Sodium benzoate | 0.4 | 0.4 | 0.4 | 0.4 | 0.4 | 0.4 |
| Lactic acid | 0.1 | 0.1 | 0.1 | 0.1 | 0.1 | 0.1 |
| Citric acid | 0.4 | 0.4 | 0.4 | 0.4 | 0.4 | 0.4 |
| Perfume oil | 1.3 | 1.3 | 1.3 | 1.3 | 1.3 | 1.3 |
| Water | 67.3 | 67.3 | 67.3 | 71.3 | 72.3 | 68.3 |
| NaCl | 0.2 | 0.2 | 0.2 | 0.2 | 0.2 | 0.2 |
| Foaming behavior | 2.9 | 2.1 | 1.8 | 2.0 | 2.0 | 1.9 |
| Foam volume | 3.0 | 2.3 | 2.0 | 2.0 | 2.0 | 1.9 |
| Creaminess, fine-bubble character | 3.5 | 2.2 | 2.5 | 2.1 | 2.1 | 2.1 |
| Viscosity Pa.s (20° C.) Haake Rotovisko, Spindle 2 | 9.5 | 4.0 | 15.4 | <1.0 | <1.0 | 6.1 |

What is claimed is:

1. A foaming liquid aqueous body-cleansing composition comprising:
   (a) from 3 weight percent to 30 weight percent based on the total weight of the composition, of an anionic surfactant, wherein the anionic surfactant comprises an alkyl sulfate in the ammonium or alkanolammonium salt form, or an alkyl ether sulfate, alkyl ether carboxylate acyl sethionate, acyl sarcosinate, or acyl taurine with linear alkyl or acyl groups containing 12 to 18 carbon atoms in the alkali metal or ammonium salt form, or mixtures thereof;

(b) an alkyl glycoside, an alkyl oligoglycoside or mixtures thereof;
(c) a zwitterionic surfactant corresponding to formula I:

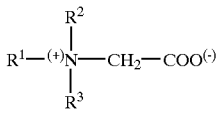
(I)

wherein $R^1$ is an alkyl or alkenyl group containing 12 to 18 carbon atoms or a $R^5$—CONH—$(CH_2)_n$ group, wherein $R^5$ is an alkyl or alkenyl group containing 12 to 18 carbon atoms and n is a number of from 2 to 4, and $R^2$ and $R^3$ are alkyl groups containing 1 to 4 carbon atoms or hydroxyalkyl groups containing 2 or 3 carbon atoms; and
(d) an ampholytic surfactant corresponding to formula II:

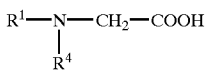
(II)

wherein $R^1$ is an alkyl or alkenyl group containing 12 to 18 carbon atoms or a $R^5$—CONH—$(CH_2)_n$ group, wherein $R_5$ is an alkyl or alkenyl group containing 12 to 18 carbon atoms and n is a number of from 2 to 4, and $R^4$ is an alkyl group containing 1 to 4 carbon atoms or an hydroxyalkyl group containing 2 or 3 carbon atoms, wherein the weight ratio of (a) (b) to is 10:(0.5 to 5):, and wherein the weight ratio of the zwitterionic surfactant (c) to the ampholytic surfactant (d) is from 1:(0.1 to 0.5).

2. The composition of claim 1 wherein the anionic surfactant comprises an alkyl ether sulfate corresponding to formula (III):

$$R^6O(C_2H_4O)_m—SO_3^{(-)}M^{(+)} \quad \text{(III)}$$

wherein $R^6$ is an alkyl or alkenyl group containing 12 to 18 carbon atoms, m is a number of from 1 to 4 and $M^{(+)}$ is an alkali metal, magnesium, ammonium or alkanol ammonium ion.

3. The composition of claim 2 comprising at least 5 percent by weight of the alkyl ether sulfate.

4. The composition of claim 1 wherein the alkyl glycoside or alkyl oligoglycoside corresponds to the formula $R^7(G)_x$, wherein $R^7$ is a linear alkyl group containing 8 to 16 carbon atoms and $(G)_x$ is a glucoside or an oligoglucoside unit with a degree of oligomerization x, of from 1 to 2.

5. The composition of claim 1 wherein the zwitterionic surfactant (c) comprises a cocoamidopropyl betaine, wherein $R^1$ of formula (I) is a $R^5$CONH—$(CH_2)_3$— group, wherein $R^5$CO is derived from a $C_{12-18}$ cocofatty acid or palm kernel oil fatty acid, and $R^2$ and $R^3$ are methyl groups.

6. The composition of claim 1, wherein the ampholytic surfactant (d) comprises a cocoamphoglycinate wherein $R^1$ of formula (II) is a $R^5$CONH—$(CH_2)_3$— group wherein $R^5$CO is derived from a $C_{12-18}$ cocofatty acid or palm kernel oil fatty acid, and $R^4$ is a hydroxy ethyl group.

7. The composition of claim 1 comprising less than 30 percent by weight of water.

8. The composition of claim 1 comprising less than 5 percent by weight of the anionic surfactant (a).

9. The composition of claim 1 comprising 5 to 20 percent by weight of the anionic surfactant (a).

* * * * *

UNITED STATES PATENT AND TRADEMARK OFFICE
CERTIFICATE OF CORRECTION

PATENT NO.    : 6,391,834 B1
DATED         : May 21, 2002
INVENTOR(S)   : Heike Schelges et al.

It is certified that error appears in the above-identified patent and that said Letters Patent is hereby corrected as shown below:

Column 4,
Line 64, delete "sethionate", and insert therefor -- isethionate --.

Column 5,
Line 26, delete "$R_5$", and insert therefor -- $R^5$ --.
Line 30, after "(a)", insert -- to --.
Line 30, after "(b) to", insert -- [(c) + (d)] --.
Line 31, after "to 5):", insert -- [1 to 5] --.

Signed and Sealed this

Ninth Day of September, 2003

JAMES E. ROGAN
*Director of the United States Patent and Trademark Office*